United States Patent [19]

Takamura

[11] Patent Number: 4,831,456
[45] Date of Patent: May 16, 1989

[54] IMAGING APPARATUS USING A SOLID-STATE IMAGING ELEMENT HAVING A SUBSTRATE

[75] Inventor: Koji Takamura, Tokyo, Japan

[73] Assignee: Olympus Optical Co., Ltd., Tokyo, Japan

[21] Appl. No.: 113,824

[22] Filed: Oct. 26, 1987

[30] Foreign Application Priority Data

Dec. 8, 1986 [JP] Japan .................................. 61-292042
Sep. 4, 1987 [JP] Japan .................................. 62-221436

[51] Int. Cl.$^4$ .............................................. H04N 7/18
[52] U.S. Cl. ...................................... 358/229; 358/98
[58] Field of Search .................. 358/98, 229, 213.11, 358/209

[56] References Cited

U.S. PATENT DOCUMENTS

| | | |
|---|---|---|
| 2,764,149 | 9/1956 | Sheldon . |
| 4,491,865 | 1/1985 | Danna et al. . |
| 4,639,772 | 1/1987 | Sluyter et al. ........................ 358/98 |
| 4,677,471 | 6/1987 | Takamura et al. .................... 358/98 |
| 4,745,470 | 5/1988 | Yabe et al. ............................ 358/98 |
| 4,745,471 | 5/1988 | Takamura et al. .................... 358/98 |

FOREIGN PATENT DOCUMENTS

| | | |
|---|---|---|
| 3542761 | 6/1986 | Fed. Rep. of Germany . |
| 3600283 | 7/1986 | Fed. Rep. of Germany . |
| 3410401 | 10/1986 | Fed. Rep. of Germany . |
| 60-208726 | 10/1985 | Japan . |
| 62-40414 | 2/1987 | Japan . |

Primary Examiner—Edward L. Coles, Sr.
Assistant Examiner—Victor R. Kostak
Attorney, Agent, or Firm—Frishauf, Holtz, Goodman & Woodward

[57] ABSTRACT

An imaging apparatus includes a camera head and a camera control unit. An objective optical system is arranged at a front end portion of the camera head. A solid-state imaging device having a first external terminal group to or from which signals subjected to signal processing inside the camera head are input or output, and a second external terminal group, which is separated from the first external terminal group, and to or from which signals that are not subjected to signal processing inside the camera head are input or output, is arranged behind the objective optical system. A circuit board has at least two connecting terminal groups. One connecting terminal group of the circuit board is connected to the first external terminal group, and the other connecting terminal group is connected to one end portion of a first conductive wire group of a power cable. One end portion of a second conductive wire group of the power cable is connected to the second external terminal group. The other end portion of each of the first and second conductive wire groups is connected to the camera control unit. Therefore, the camera head can be rendered compact.

27 Claims, 13 Drawing Sheets

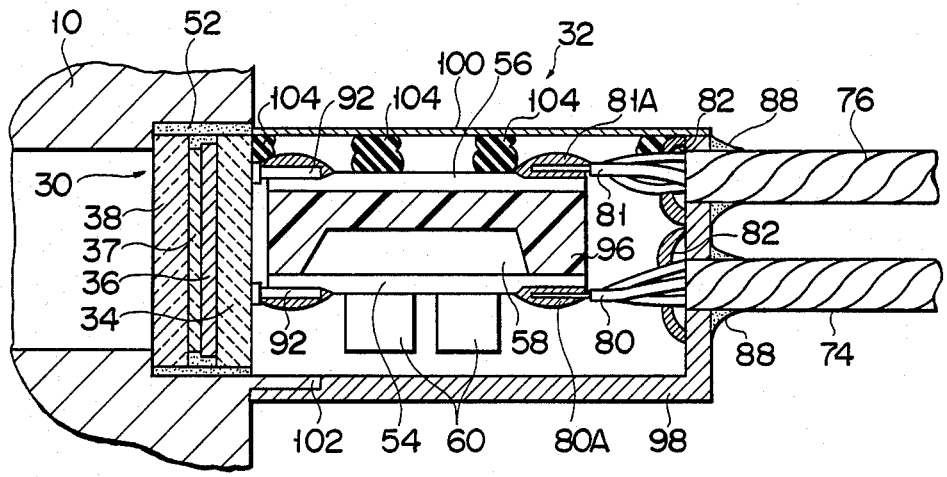
F I G. 8
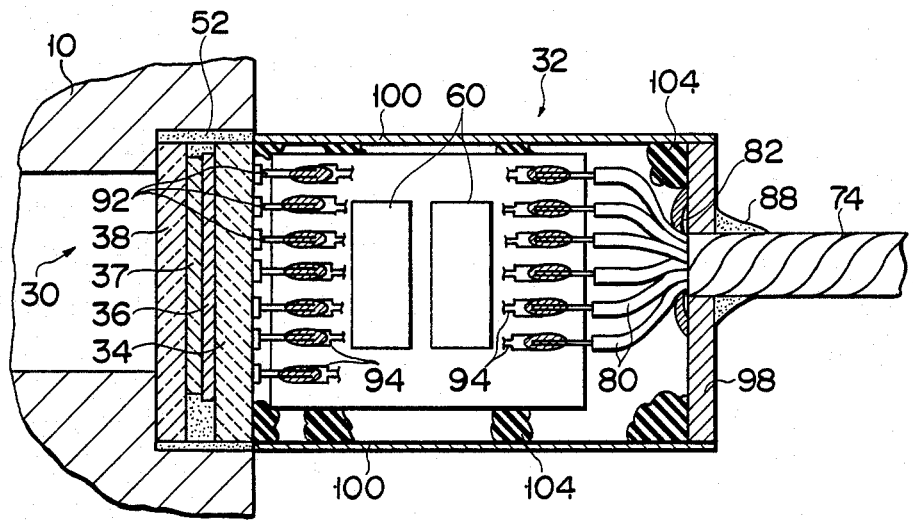
F I G. 9

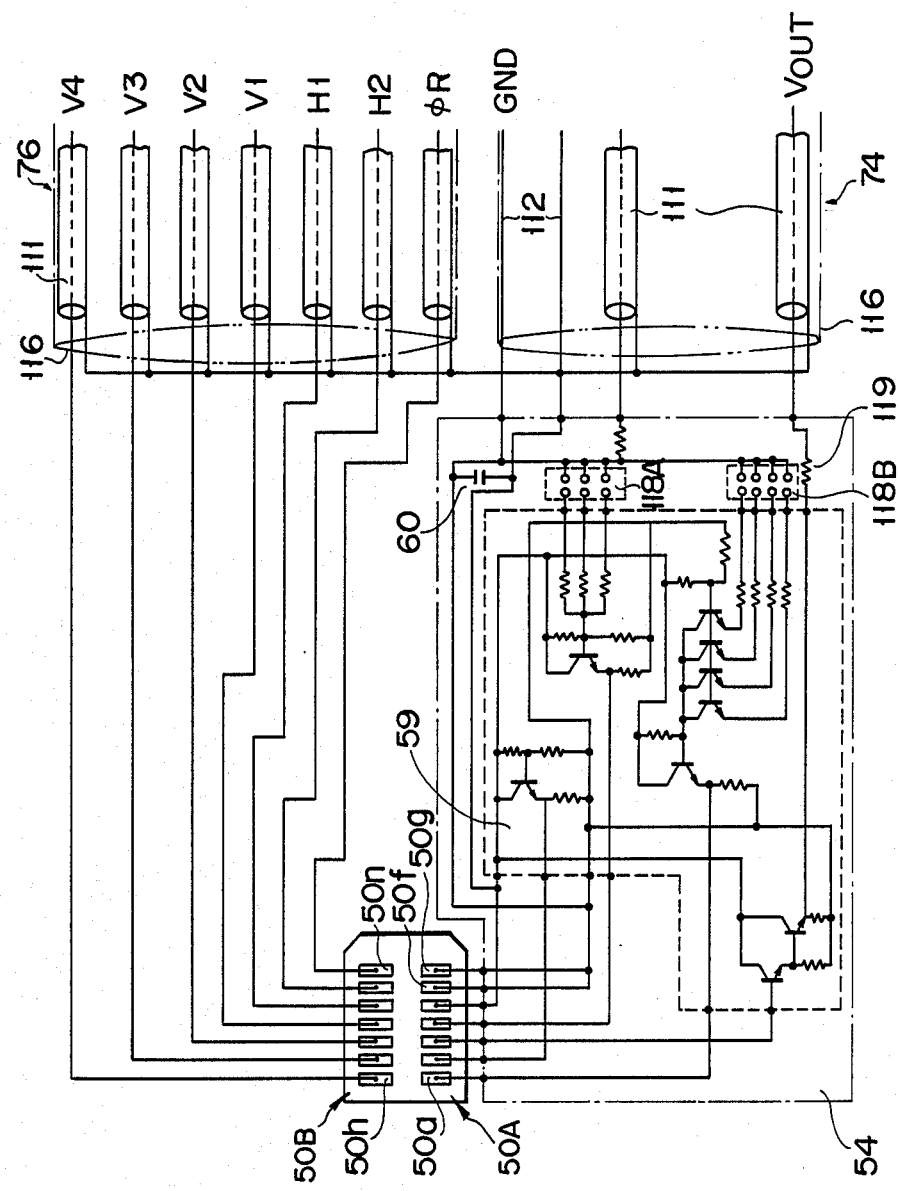
F I G. 14

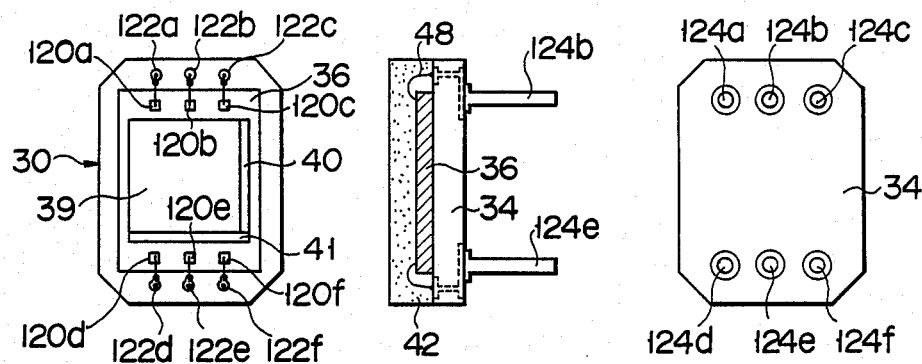
F I G. 18    F I G. 19    F I G. 20
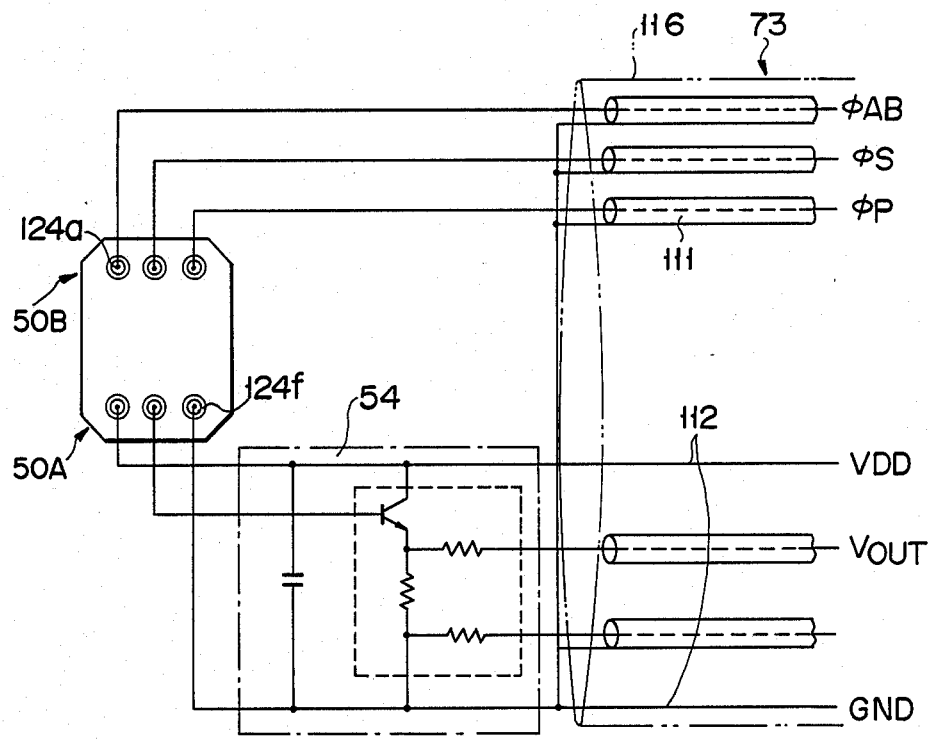
F I G. 21

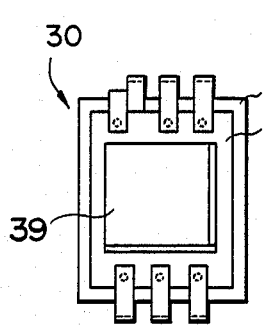
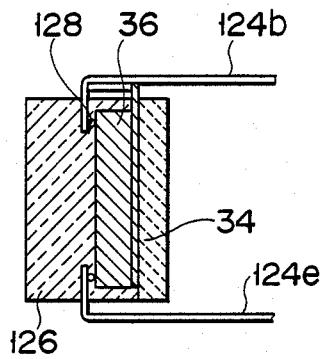
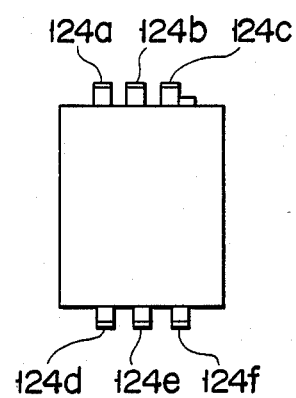
F I G. 22   F I G. 23   F I G. 24
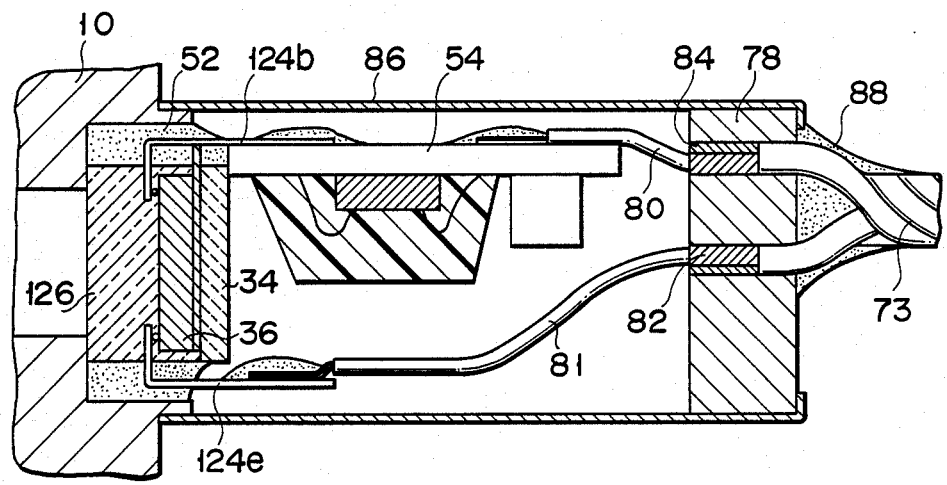
F I G. 25

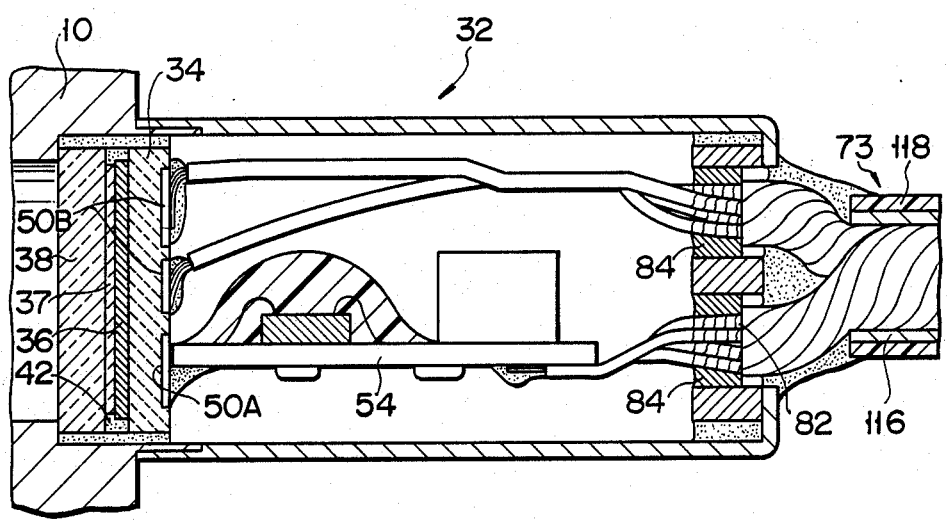
F I G. 26
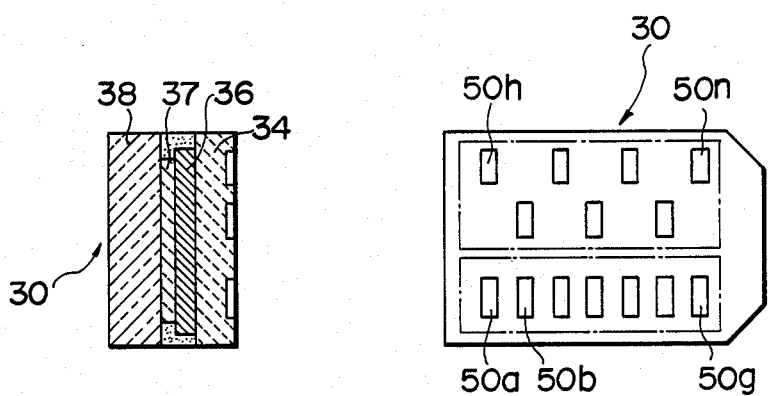
F I G. 27    F I G. 28

IMAGING APPARATUS USING A SOLID-STATE IMAGING ELEMENT HAVING A SUBSTRATE

BACKGROUND OF THE INVENTION

A. Field of the Invention

The present invention relates to an imaging apparatus such as an endoscope or a monitor TV camera which comprises a solid-state imaging device in a camera head.

B. Description of the Prior Art

An endoscope, a so-called electronic scope, is known as a conventional imaging apparatus. In this endoscope, a solid-state imaging device (SID) is arranged in the distal end portion of an insertion section, and an optical image received by the light-receiving surface of the SID can be monitored through a camera control unit.

An endoscope comprising a camera head incorporating such an SID is disclosed in Japanese Patent Disclosure No. 60-208726. In an endoscope of this type, an SID chip is arranged to be perpendicular to the axis of an endoscope insertion section, and external terminals are randomly arranged on the rear surface of the SID. All the external terminals are connected to circuit boards mounting electrical parts. Conductive wire groups of a power cable connecting a camera control unit and the camera head, are connected to all the circuit boards mounting the electrical parts, and are also connected to the external terminals of the SID.

In an electrical signal processing section in the camera head in which external terminals are randomly arranged and all the terminals are connected to peripheral circuits as in the conventional SID, if the number of I/O signals is small and only several shield wires are connected like in a black-white SID, there is no problem. However, if several tens of shield wires must be connected, a considerably large space for connecting the SID and circuit boards and for connecting circuit boards and the shield wires is required, and the size of the peripheral circuit board becomes undesirably large. For this reason, the entire electrical signal processing section becomes bulky and prevents a compact camera head. In the endoscope, this undesirably causes an increase in outer diameter of the insertion section.

SUMMARY OF THE INVENTION

It is an object of the present invention to provide an imaging apparatus comprising a compact camera head.

The object of the present invention can be achieved by the following imaging apparatus. More specifically, the imaging apparatus of the present invention comprises a camera head and a camera control unit. An objective optical system is arranged at the front end portion of the camera head, and a solid-state imaging device including a first external terminal group of terminals to or from which signals processed inside the camera head are input or output, and a second external terminal group, which is separated from the first external terminal group, and including terminals to or from which signals that are not processed inside the camera head are input or output, is arranged behind the objective optical system. One connecting terminal group of a circuit board which has at least two connecting terminal groups is connected to the first external terminal group. The other connecting terminal group of the circuit board is connected to one end portion of a first conductive wire group of a power cable. One end portion of a second conductive wire group of the power cable is connected to the second external terminal group. The other end portion of each of the first and second conductive wire groups is connected to the camera control unit.

The circuit board is coupled to only the external terminals of the first group, not to all external terminals. It can therefore be relatively small. Further, since no signal exchange is required between the two separated groups of external terminals, the wiring inside the electrical signal processing section is simple and requires but a small space.

As has been described, the power cables are divided into two groups. The layout of these cables is therefore simple, and does not require dead space.

On the circuit board, there are mounted electronic parts, such as ICs, capacitors, resistors, and transistors, used to amplify the video signals output from the SID, stabilize the voltage applied to the SID, prevents the reflection of signals due to the matching between the camera head and the power cables, and remove noise from the signals.

BRIEF DESCRIPTION OF THE DRAWINGS

FIGS. 8 and 9 are longitudinal sectional views showing a first modification of the camera head section of the imaging apparatus according to the first embodiment;

FIG. 14 is a view showing a wiring state in the camera head;

FIGS. 18 to 20 are respectively a front view, a longitudinal sectional view, and a bottom view showing a first modification of the solid-state imaging device;

FIG. 21 is a schematic view showing the solid-state imaging device and an electrical circuit shown in FIGS. 18 to 20;

FIGS. 22 to 24 are respectively a front view, a longitudinal sectional view, and a bottom view showing a second modification of the solid-state imaging device;

FIG. 25 is a longitudinal sectional view showing a camera head incorporating the solid-state imaging device illustrated in FIGS. 22 to 24;

FIG. 26 is a longitudinal sectional view showing another modification of the camera head section of the imaging apparatus according to the second embodiment;

FIGS. 27 and 28 are respectively a longitudinal sectional view and a rear view, showing the solid-state imaging device illustrated in FIG. 26;

DETAILED DESCRIPTION OF THE PREFERRED EMBODIMENTS

Figure 1:
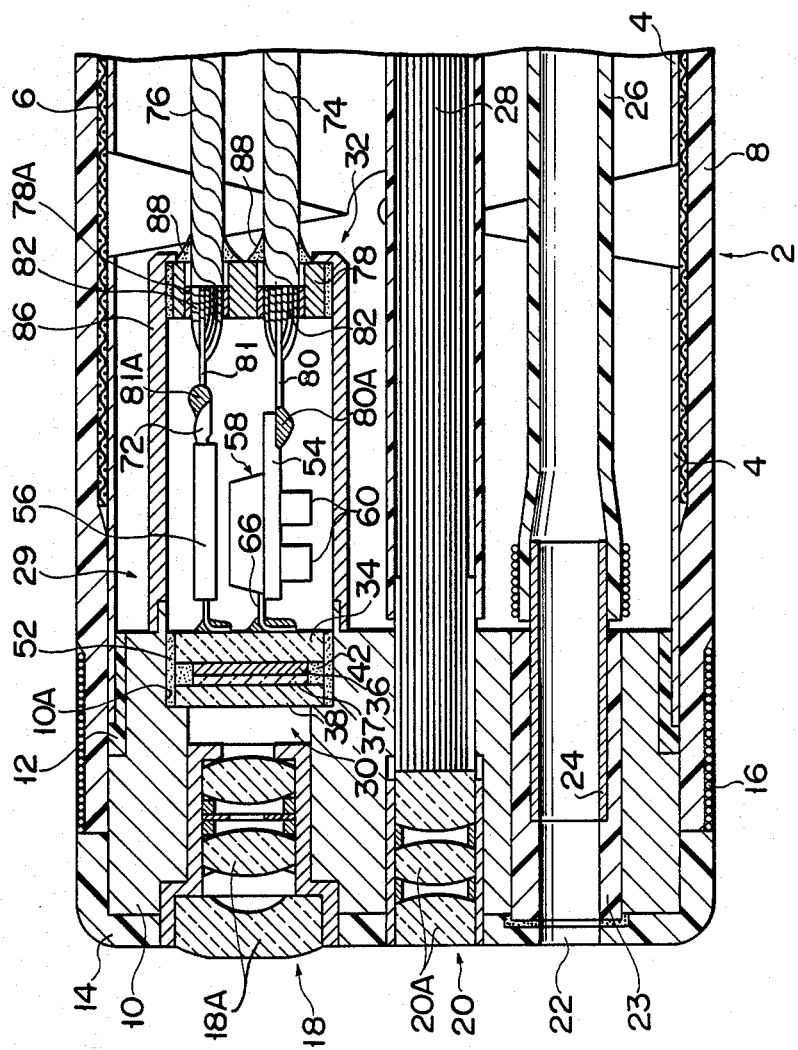
FIG. 1 is a longitudinal sectional view showing an endoscope comprising an imaging apparatus according to a first embodiment of the present invention.

FIG. 1 shows the structure of a distal end portion of an insertion section of an endoscope or an electronic scope comprising an imaging apparatus according to the present invention. The insertion section of the endoscope comprises bending section 2. A plurality of tubular segments 4 which are rotatably coupled to each other are arranged in bending section 2. The outer surface of each tubular segment 4 is covered by braid 6 and rubber sheath 8. Metal distal end member 10 is coupled to tubular segment 4 arranged in the distal end portion via insulating member 12. An exposed portion of distal end member 10 is covered with insulating cover 14 and sheath 8. Distal end member 10 and sheath 8 are connected by threaded adhesive layer 16.

A plurality of mounting holes ar formed in distal end member 10 and insulating cover 14 arranged at the distal end of the insertion section. Objective optical system 18 and illumination optical system 20 are fitted in the mounting holes. Forceps channel 22 is constituted by pipe-like insulating member 23 fitted in the mounting hole of distal end member 10, forceps channel pipe 24 engaged with the rear opening portion of the inner hole of insulating member 23, and forceps channel tube 26 coupled to the rear end portion of pipe 24 and extending inside the insertion section. Illumination optical system 20 having a plurality of optical lenses 20A are optically connected to the distal end surface of light guide fiber 28 inserted through the insertion section. Solid-state imaging device (SID) 30 constituting camera head section 29 of the imaging apparatus, and electrical signal processing section 32 connected to SID 30 are arranged behind objective optical system 18 having a plurality of objective lenses 18A. Therefore, living tissues in a body cavity are observed using SID 30, and diseased tissues can be simultaneously treated using forceps inserted in channel 22.

Figures 4, 5:
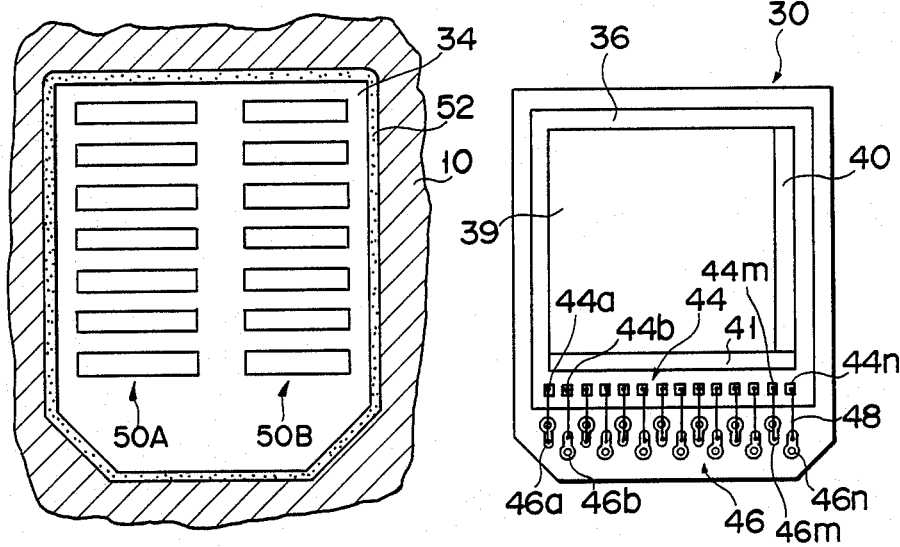
FIG. 4 is a cross-sectional view taken along a line A—A in FIG. 3.
FIGS. 5 to 7 are respectively a front view, a longitudinal sectional view, and a rear view showing a solid-state imaging device according to the first embodiment.
Figures 6, 7:
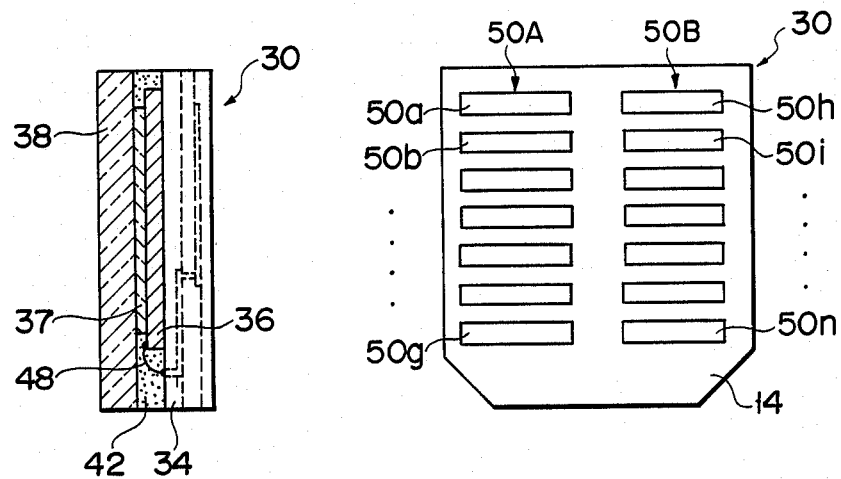

SID 30 will now be described. SID 30 is illustrated in detail in FIGS. 5 to 7. As shown in FIG. 6, SID chip 36, color filter array 37, and cover glass 38 are sequentially stacked on base 34 formed of a ceramic multi-layered substrate, and are packaged by seal member 42. More specifically, SID chip 36 comprises image area 39, optical black 40, and horizontal shift register 41, and is die-bonded to the surface of base 34. Chip electrodes 44 of SID chip 36 and bonding pads 46 with through holes formed on base 34 are connected through bonding wires 48. Bonding pads 46 are connected to flat leads consisting of first and second external terminal groups 50A, 50B formed on the bottom surface of base 34. Color filter array 37 and cover glass 38 are sequentially stacked on the upper surface of SID chip 36, and these components are packaged by seal member 42.

SID 30 with the above structure is arranged to be perpendicular to the axis of the insertion section of the endoscope, i.e., perpendicular to the optical axis of objective optical system 18 in recess 10A formed in the rear end portion of distal end member 10. SID 30 is fixed by adhesive layer 52 so that its light receiving surface faces objective optical system 18.

Figure 2:
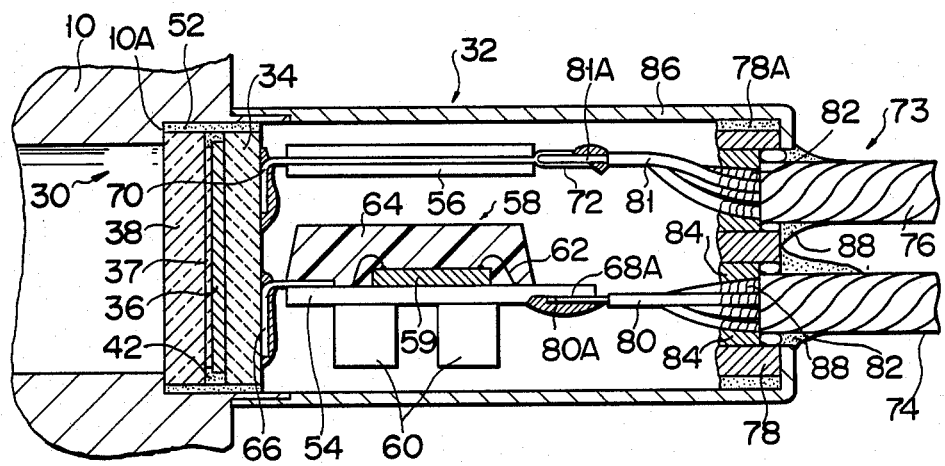
FIGS. 2 and 3 are longitudinal sectional views showing a camera head section of the imaging apparatus illustrated in FIG. 1.

Electrical signal processing section 32 comprises first circuit board 54 on the upper and lower surfaces of which electrical parts are mounted, and second circuit board 56 on which only a conductive pattern is formed. More specifically, IC 58 is arranged on the upper surface of first circuit board 54, and capacitors 60 are mounted on the lower surface. In particular, IC 58 employs a compact package structure, as shown in FIG. 2. More specifically, bare chip 59 is directly die-bonded to first circuit board 54. Bare chip 59 and circuit board 54 are connected through bonding wires 62. A portion around bare chip 59 is sealed by IC seal member 64.

A large number of L-shaped board lead legs 66 are bonded on the upper surface of one edge portion of first circuit board 54, and a large number of grooves 68A are formed on the lower surface of the other edge portion of board 54. Shield wire connecting land 68 is provided to each groove. Bare chip 59 and capacitors 60 are connected to some of lead legs 66 and some of shield wire connecting leads 68.

A large number of L-shaped board lead legs 70 are formed on one end portion of second circuit board 56, and pipe-shaped terminals 72 through which lead wires are inserted are formed on the other end portion thereof. A wiring pattern is formed on the entire surface of board 56, and is connected to lead legs 70 and pipe-shaped terminals 72. An open end portion of each terminals 72 is obliquely cut so that a lead wire can be easily inserted therein.

Figure 3:
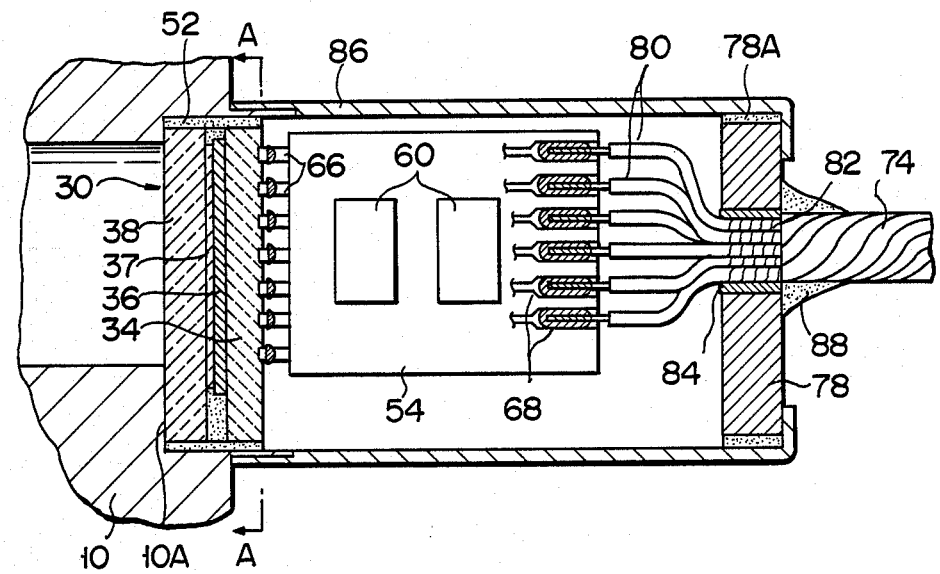

As shown in FIG. 3, first and second circuit boards 54 and 56 are less broad than SID 30. First and second circuit boards 54 and 56 extend to be vertically shifted and parallel to each other. Lead legs 66 and 70 of boards 54 and 56 are soldered to flat leads 50. Boards 54 and 56 are arranged along the axial direction of the insertion section.

Power cable 73 inserted through the insertion section is divided into first bundle 74 of shield wires and second bundle 76 of shield wires. Each shield wire is soldered to corresponding lead 68 or terminal 72. For example, when twelve shield wires are connected to the circuit boards, the shield wires are divided into two bundles 74 and 76 of shield wires, and bundles 74 and 76 are inserted in through holes of shield wire holder 78. Then, shield wire inner conductors 80 and 81 covered with insulating tubes are exposed from the bundles of shield wires. Then, conductor 80A of each shield wire inner conductor 80 in first bundle 74 of shield wires is soldered to lead 68, and conductor 81A of each shield wire inner conductor 81 in second bundle 76 of lead wires is inserted through corresponding pipe-shaped terminal 72 and is soldered thereto. Outer conductors 82 of bundles 74 and 76 of shield wires are bonded to shield wire holder 78 by solder layer 84. Holder 78 is bonded inside the proximal end portion of metal shield cover 86 arranged to surround circuit boards 54 and 56 by conductive adhesive layer 78A. Holder 78 is electrically connected to shield cover 86. A distal end portion of shield cover 86 is electrically connected to metal distal end member 10. Therefore, the entire electrical signal processing section 32 can be shielded. First and second bundles of lead wires 74 and 76 are adhered to holder 78 by adhesive 88, thereby reinforcing contacting portions.

As described above, in the endoscope comprising the imaging apparatus according to the present invention, circuit boards 54 and 56 are arranged along the axial direction of the insertion section. Therefore, if the number of shield wires or electrical components is increased, boards 54 and 56 need only be extended in the axial direction of the insertion section. Therefore, processing section 32 will not become larger than the radial size of the package of SID 30. For this reason, the layout of components such as light guide fiber 28, forceps channel tube 26, and the like is not interfered by the circuit boards connected to the SID, and an insertion section with a thin distal end portion can be formed. Since soldered portions are concentrated on specific portions of circuit boards 54 and 56, a wiring operation can be facilitated.

The imaging apparatus according to the first embodiment of the present invention has the following advantages. More specifically, since lead legs 66 and 70 are provided to the edge portions of boards 54 and 56, manufacture of parts can be facilitated as compared to a case wherein lead legs 66 and 70 are arranged on the rear surface of SID 30. Since metal shield cover 86 is used as a support member for power cable 73, power cable 73 can be reliably supported. Since conductors 80 can be connected only by inserting them into pipe-shaped terminals 72, the wiring operation of the shield wires can be facilitated. Since the shield wires are divided into two bundles, the layout of the cable inside the insertion section of the endoscope can be easily performed. Therefore, the diameter of the insertion section can be decreased, and the resistance of the cable when the bent section is repetitively bent can be improved. In addition, since electrical parts are mounted on circuit board 54 as a bare chip, the circuit board can be rendered compact, and hence, the entire electrical signal processing section 32 can also be rendered compact. Processing section 32 can be perfectly shielded by distal end member 10, shield cover 86, shield wire holder 78, and outer conductors 82, and is satisfactorily protected from noise. Since the shield members are insulated from external metal members at the distal end portion such as tubular segment 4, braid 6, channel pipe 24, and the like, electrical safety can be ensured.

A first modification of a camera head section will be described with reference to FIGS. 8 and 9. In this modification, the connecting structure and the shield structure of circuit boards 54 and 56 are different from those of the first embodiment. More specifically, a plurality of lead legs 92 in two horizontal lines project from the bottom surface of SID 30 which are vertically shifted from each other. First and second circuit boards 54 and 56 each having flat lands 94 at two edge portions are integrally bonded to each other by substrate integrating member 96. One end portion of the integrated circuit board is inserted between upper and lower lead legs 9 and is soldered thereto.

Therefore, since lead legs 92 are provided to SID 30, circuit boards 54 and 56 can be easily aligned to SID 30. Since boards 54 and 56 are integrally bonded to each other, they can be easily fixed to SID 30, thus improving workability.

Projection 102 projects from the rear end portion of distal end member 10. L-shaped support member 98 having a shield wire holding portion is mounted on projection 102. Member 98 is formed of a metal, and is electrically connected to member 10. The upper and two side surfaces of support member 98 are covered with conductive film 100, and insulating filler 104 for holding conductive film 100 is provided inside film 100.

Therefore, in the first modification, since the entire processing section 32 is not shielded by a hard member unlike in the first embodiment, a space necessary for shielding can be reduced. As a result, processing section 32 can be rendered compact.

Figure 10:
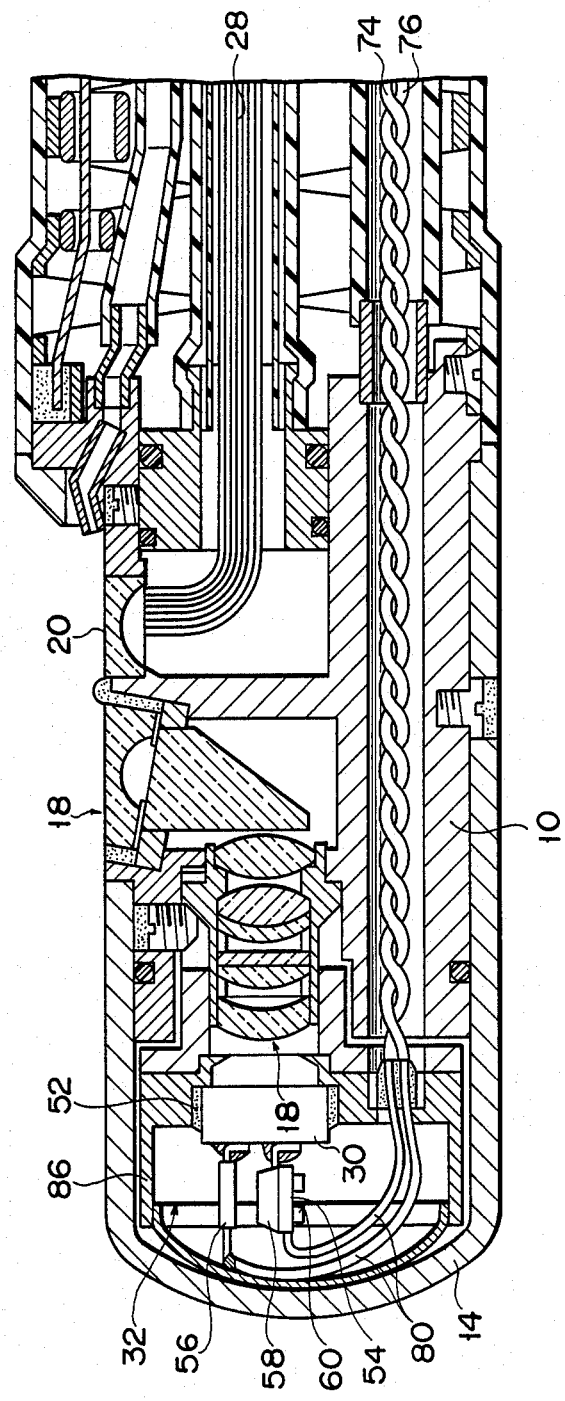
FIG. 10 is a longitudinal sectional view showing a second modification of the camera head section of the imaging apparatus according to the first embodiment.
Figure 11:
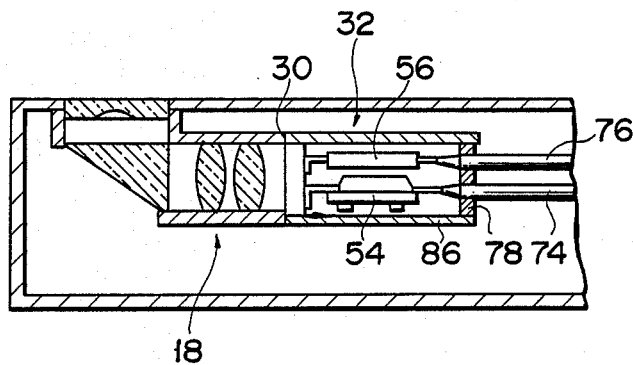
FIG. 11 is a longitudinal sectional view showing a third modification of the camera head section of the imaging apparatus according to the first embodiment.

FIGS. 10 and 11 show another modification of the camera head section. In this modification, the electrical signal processing section of the camera head section according to the first embodiment of the present invention is applied to a side-view type endoscope.

As shown in FIG. 10, SID 30 is incorporated in the front portion of distal end member 10. The light receiving surface of SID 30 is arranged to face the front surface of objective optical system 18 arranged therebehind. First circuit board 54 mounting electrical parts and second circuit board 56 on which only a wiring pattern is formed are arranged to be parallel to each other along the axial direction of the insertion section of the endoscope.

As shown in FIG. 11, in the side-view type endoscope, SID 30 and processing section 32 may be arranged behind objective optical system 18.

A second embodiment of an imaging apparatus according to the present invention will now be described with reference to FIGS. 12 to 17.

Figure 12:
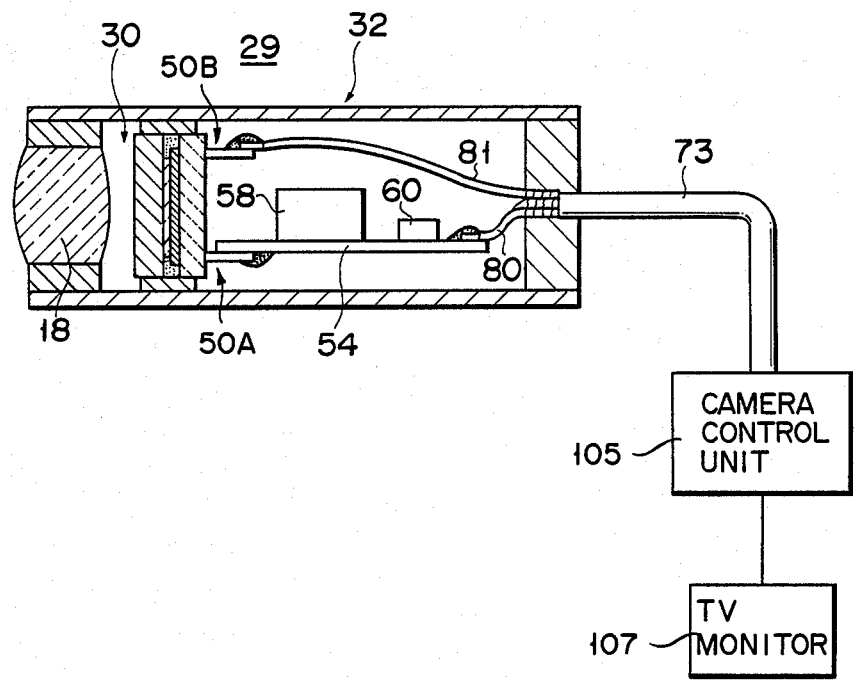
FIG. 12 is a longitudinal sectional view schematically showing a imaging apparatus according to a second embodiment of the present invention.

As shown in FIG. 12, electrical signal processing section 32 in camera head 29 according to the second embodiment comprises only first circuit board 54 on which electrical parts are mounted. IC 58 and capacitors 60 are mounted on the upper surface of board 54. Power cable 73 connected to camera head 29 is connected to camera control unit (CCU) 105. CCU 105 is connected to TV monitor 107.

Figure 13:
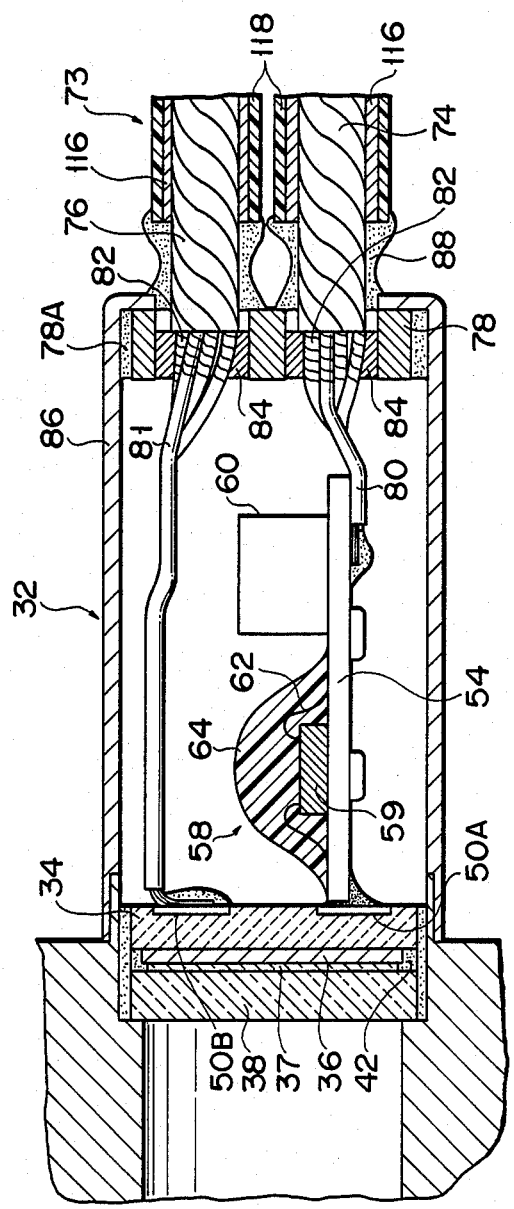
FIG. 13 is a longitudinal sectional view showing a camera head section of the imaging apparatus according the second embodiment.

As shown in FIG. 13, IC 58 employs a compact package structure. Bare chip 59 is bonded onto first circuit board 54. Chip 59 and board 54 are connected through bonding wires 62. A portion around chip 59 is sealed by IC seal member 64.

Power cable 73 is divided, over the overall length of the power cable, into first bundle 74 of shield wires including signal lines subjected to signal processing inside the camera head, and second bundle 76 of shield wires consisting of signal lines which are not subjected to signal processing, and the bundles are respectively inserted in two through holes of cable holder 78. Shield wire inner conductors 81 of bundle 76 are directly connected to terminals 50h to 50n (shown in FIG. 7) which are not subjected to signal processing inside processing section 32, i.e., the camera head. Shield wire inner conductors 80 of bundle 74 are connected to terminals formed on the rear end portion of first circuit board 54.

Wiring of the electrical signal processing section according to the second embodiment will be explained hereinafter with reference to a wiring pattern in processing section 32 illustrated in FIG. 14.

A reset pulse terminal ($\phi$R) of SID chip 36 is connected to ($\phi$R) of shield wire 111 through chip electrode 44a, bonding pad 46, and flat lead 50n.

A power supply terminal (VDD) of SID chip 36 is connected to (VDD) of simple wire 112 through chip electrode 44b, bonding pad 46b, flat lead 50e, and first circuit board 54.

A video output terminal (Vout) is connected to a shield wire (Vout) through chip electrode 44c, bonding pad 46c, flat lead 50c, and first circuit board 54.

A load gate terminal (LG) (a constant current source for an output buffer, i.e., an applied voltage line for setting a current value upon transfer) is connected to first circuit board 54 through chip electrode 44d, bonding pad 46d, and flat lead 50b.

An output gate terminal (OG) (an output line for an output buffer) is connected to first circuit board 54 through chip electrode 44e, bonding pad 46e, and flat lead 50b.

In terminals (H1, H2) for horizontal clock pulses (1) and (2) as a CCD transfer group, the terminal for the horizontal clock pulse (1) is connected to a shield wire (H1) through chip electrode 44f, bonding pad 46f, and flat lead 50m, and the terminal for the horizontal clock pulse (2) is connected to a shield wire (H2) through chip electrode 44g, bonding pad 46g, and flat lead 50l.

A test terminal (IG) which is used for testing a CCD before it is incorporated in the camera head and is used as a GND terminal after testing is connected to first circuit board 54 through chip electrode 44f, bonding pad 46h, and flat lead 50f.

In terminals (V1, V2, V3, V4) for vertical clock pulses (1), (2), (3), and (4) as a CCD transfer group, the terminal for the vertical clock pulse (1) is connected to a shield wire (V1) through chip electrode 44i, bonding pad 46i, and flat lead 50k. The terminal for the vertical clock pulse (2) is connected to a shield wire (V2) through chip electrode 44j, bonding pad 46j, and flat lead 50i. The terminal for the clock pulse (3) is connected to a shield wire (V3) through chip electrode 44k, bonding pad 46k, and flat lead 50j. The terminal for the vertical clock pulse (4) is connected to a shield wired (V4) through chip electrode 44l, bonding pad 46l, and flat lead 50h.

A terminal (PW) connected to an electrode of an intermediate layer of a CCD wafer is connected to first circuit board 54 through chip electrode 44m, bonding pad 46m, and flat lead 50g.

A substrate power supply terminal (Vsub) connected to an electrode of a lowermost layer of the CCD wafer is connected to first circuit board 54 through chip electrode 44n, bonding pad 46n, and flat lead 50a.

Flat leads 50h to 50n to which terminals φR, H1, H2, V1, V2, V3, and V4 of SID chip 36 are connected, are terminals which receive signals that need not be processed inside the camera head. These leads are arranged in line on one side of base 14, and are directly connected to the inner conductors of shield wires. Flat leads 50a to 50g connected to terminals VDD, Vout, LG, OG, IG, PW, and Vsub of chip 36 are terminals to or from which signals that must be processed inside the camera head are input or output. These leads are connected to the terminals of circuit board 54.

Selection terminals 118A and 118B of circuit board 54 shown in FIG. 14 are used for adjusting variations in drive voltages (OG) and (Vsub) during manufacture of the SID, and connections between terminals are selected in accordance with characteristics of individual SIDs.

The IG terminal (50f) and the PW terminal (50g) of SID chip 36 are used for testing the electrical performance of the SID chip itself. In a mounting state after the test, these terminals are electrically connected to each other on circuit board 54.

A dummy cable connected to circuit board 54 is used for removing noise components of the Vout cable. More specifically, noise components of the Vout cable can be removed by utilizing the fact that the noise components appearing on the dummy cable are the same as those on the Vout cable.

Figure 15:
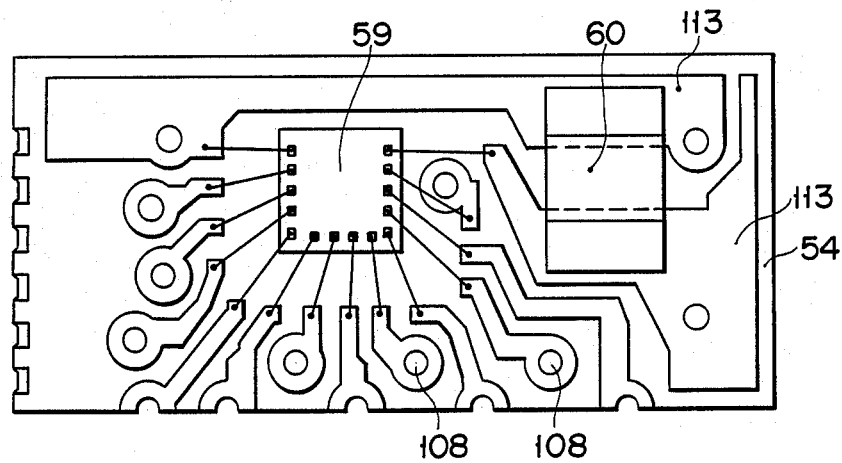
FIGS. 15 to 17 are respectively a plan view, a side view, and a bottom view of a circuit board.
Figure 16:
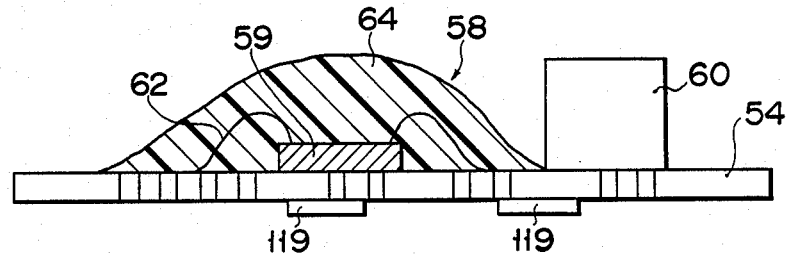
Figure 17:
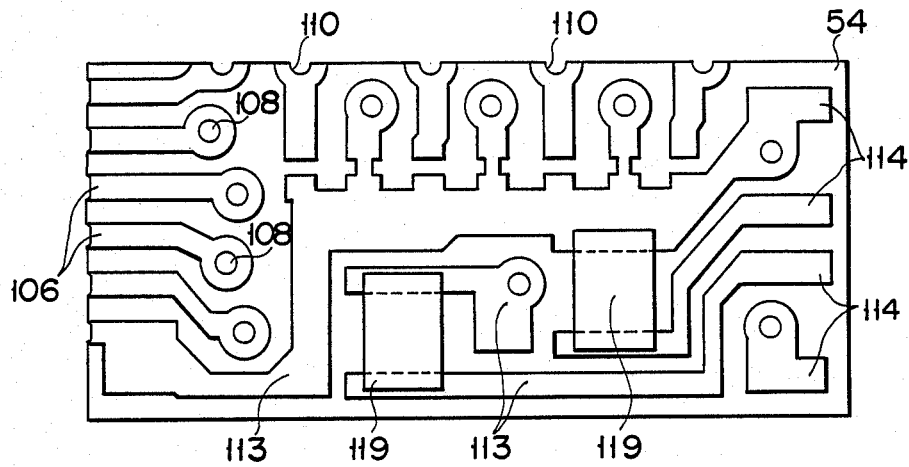

FIGS. 15, 16, and 17 illustrate circuit board 54 in detail. As shown in FIG. 17, circuit board 54 has patterns 106 connected to flat leads 50a to 50g on the left side portion, and each pattern 106 has through hole 108 for arranging and wiring an electrical part on circuit board 54. In order to make circuit board 54 compact, side-surface through holes 110 are formed on the side surface of circuit board 54.

As shown in FIG. 16, a molded element is not used as IC 58, and bare chip (IC chip) 59 is attached onto circuit board 54 and is connected to the patterns on circuit board 54 by bonding wires 62. IC chip 59 and the connecting portions are sealed by IC seal member 64 in order to protect them from an outer atmosphere.

Patterns 114 for connecting inner conductors 80 of shield wires 111 and simple wires 112 are provided on the right side portion of circuit board 54.

As shown in FIGS. 13 and 14, first bundle of shield wires 74 consists of two coaxial shield wires 111 (Vout and dummy wires), and two simple wires 112 (GND and VDD wires). Inner conductor 80 of each shield wire 111 and each simple wire 112 are connected to patterns 114 of circuit board 54. Outer conductors 92 of shield wires 74 are electrically connected to cable holder 78.

Second bundle of shield wires 76 consists of seven coaxial shield wires 111 (V1, V2, V3, V4, H1, H2, and φR), and inner conductors 81 of shield wires 111 are directly connected to flat leads 50h to 50n of the SID, and outer conductors 82 are electrically connected to cable holder 78.

Bundles 74 and 76 of shield wires are covered by unit shield 116, and the proximal end portion of shield 116 is connected to a ground terminal (not shown) of the CCU. Shield 116 is further covered by cable protection sheath 118.

In the imaging apparatus according to the second embodiment, the wiring inside the electrical signal processing section is simplified, and the layout of the components requires a minimum space. Thus, the processing section can be rendered compact, and the entire camera head can be made compact.

No second circuit board having a wiring pattern is mounted on the terminal group of the SID for receiving signals which are not subjected to signal processing in the camera head, and the cable is directly connected to the terminal group. Thus, a soldered portion can be eliminated, and workability can be improved.

As shown in FIGS. 15 to 17, in order to concentrate circuit components for signal processing, a wiring group for receiving signals which are not subjected to signal processing in the camera head is separated from the circuit board. For this reason, the circuit can be effectively arranged at high density, and the circuit board can be further rendered compact.

A modification of a camera head section according to the second embodiment will now be described with reference to FIGS. 18 to 21.

The imaging apparatus according to the second embodiment employs a simultaneous type SID. An imaging apparatus according to this modification employs a frame-sequential type SID. Frame-sequential type SID 30 comprises base 34. SID chip 36 is die-bonded onto the upper surface of base 34. SID chip 36 has chip electrodes 120a to 120f, image area 39, optical black 40, and horizontal shift register 41. Bonding pads 122a to 122f with through holes are provided on two edge portions of the upper surface of base 34. Chip electrodes 120a to 120f and bonding pads 122a to 122f are connected through bonding wires 48. Pin-shaped leads 124a, to 124f electrically connected to bonding pads 122a to 122f project from the bottom surface of base 34.

A parallel clock pulse terminal ($\phi$P) of SID chip 36 is connected to ($\phi$P) of shield wire 111 through chip electrode 120a, bonding pad 122a, and lead 124c.

A serial clock pulse terminal ($\phi$S) is connected to a shield wire ($\phi$S) through chip electrode 120b, bonding pad 122b, and lead 124b.

An anti-blooming gate terminal ($\phi$AB) is connected to a shield wire ($\phi$AB) through chip electrode 120c, bonding pad 122c, and lead 124a.

A substrate terminal (Vsub) is connected to first circuit board 54 via chip electrode 120d, bonding pad 122d, and lead 124f.

A video output terminal (Vout) is connected to a shield wire (Vout) through chip electrode 120e, bonding pad 122e, lead 124e, and first circuit board 54.

A power supply terminal (VDD) is connected to a simple wire (VDD) through chip electrode 120f, bonding pad 122f, lead 124d, and first circuit board 54.

Leads 124a, 124b, and 124c connected to terminals $\phi$P, $\phi$S, and $\phi$AB which are not subjected signal processing in the processing section are aligned in line on one side of the rear surface of base 34. Leads 124d, 124e, and 124f connected to terminals Vsub, Vout, and VDD which are subjected signal processing in the processing section are aligned in line on the opposite side on the rear surface of base 34. Leads 124a, 124b, and 124e, are connected to the shield wires ($\phi$AB, $\phi$S, and ($\phi$P), respectively, and leads 124d, 124e, and 124f are connected to the terminals of circuit board 54.

Power cable 73 consists of two simple wires 112 (VDD and GND), and five shield wires 111 ($\phi$AB, $\phi$S, $\phi$P, Vout, and dummy), and is covered with unit shield 116. Other arrangements in this modification are the same as those in the second embodiment, and a detailed description thereof will be omitted.

A second modification will now be described with reference to FIGS. 22 to 25. In SID 30 according to the second modification, external I/O terminals 124a to 124f are arranged on the side surface of SID chip 36. The external terminals are divided into a first terminal group which are subjected to signal processing inside electrical signal processing section 32, and a second terminal group which is not subjected to signal processing inside processing section 32, and the terminal groups are separately arranged.

SID chip 36 and external I/O terminals 124a to 124f are connected by bumps 128, and the respective terminals are separated in the same manner as in SID 30 according to the first modification. The pattern on circuit board 54 is based on the circuit diagram shown in FIG. 21. A pattern for connecting terminals 124d, 124e, and 124f of SID 30 subjected signal processing inside processing section 32 to inner conductors 81 of shield wires 111 and simple wires 122 is provided on one surface of circuit board 54, and a pattern for mounting IC 58 and capacitor 60 is provided on the other surface of circuit board 54.

Cable 73 is divided into a cable group consisting of only signal lines which are not subjected to signal processing inside the camera head, and another cable group subjected to signal processing therein, immediately before cable holder 78.

Inner conductors 80 of the cable group consisting of signal lines which are not subjected to signal processing further extend from cable holder 78, and are directly connected to terminals 124d, 124e, and 124f of the SID which are not subjected signal processing in the camera head. Outer conductors 82 of shield wires 111 are soldered to cable holder 78.

FIGS. 26 to 28 show a third modification.

In the third modification, power cable 73 is not divided along the entire length of the cable but is divided into two groups immediately before electrical signal processing section 32. External terminal groups on one side of SID 30 are aligned in line in the previous embodiments and modifications. However, in this modification, a terminal group on one side is arranged in line and the other terminal group is arranged in two lines.

Each of two terminal groups of SID 30 may be aligned in two or more lines.

In an imaging apparatus according to the present invention as described above, external terminals are separated into a first external terminal group connected to a surrounding circuit inside a camera head, and a second external terminal group which are not connected thereto. Thus, a circuit board for a peripheral circuit can be designed to be compact, and the wiring inside the electrical signal processing section can be simplified. Therefore, the electrical signal processing section inside the camera head can be rendered compact, and the entire camera head can also be rendered compact.

A third embodiment of the present invention will be described with reference to FIGS. 29. Prism 134 as an optical element is arranged behind objective optical system 18, so that one surface of prism 134 is attached to the rear surface of the objective optical system, and solid-state imaging device (CCD) 30 is attached to the other surface of prism 134. Therefore, an optical image incident on objective optical system 18 is totally reflected by prism 134, and is guided toward an image area of CCD 30 arranged to be substantially parallel to the axis of camera head 29. Flat lead arrays serving as first and second external terminal groups are provided on the upper and lower surfaces at the proximal end portion of CCD 30.

Figure 29:
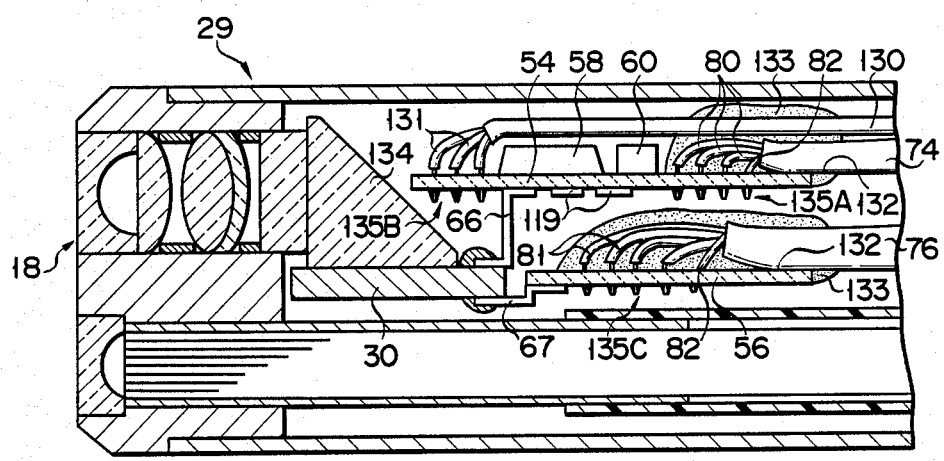
FIG. 29 is a longitudinal sectional view showing an imaging apparatus according to a third embodiment of the present invention.

As shown in FIG. 29, first circuit board 54 is arranged behind prism 134. Bent connecting leads 66 are fixed near the central portion of the lower surface of first circuit board 54 by brazing. Each connecting lead 66 is soldered to the first external terminal group on the upper surface of CCD 30. Electronic parts such as IC 58, capacitor 60, and the like are mounted on the central portion of first circuit board 54, and first and second conductive wire connecting portions 135A and 135B are formed at two edge portions of board 54. Inner and external conductors 80 and 82 of first bundle 74 of signal lines are connected to first conductive wire connecting portion 135A. Fixing portion 132 for bundle 74 of signal lines is provided on the rear portion of connecting portion 135A. The distal end portions, inner conductors 80, and external conductor 82 of first bundle 74 of signal lines are fixed to first circuit board 54 by fixing resin 133.

Second circuit board 56 is arranged to be substantially parallel to first circuit board 54 behind CCD 30. Bent connecting leads 67 are fixed to the lower surface of the distal end portion of board 56 by brazing. Each connecting lead 67 is soldered to the second external terminal group on the lower surface of CCD 30. Inner and external conductors 81 and 82 of second bundle of signal lines 76 are connected to conductor connecting portion 135C of second circuit board 56. Fixing portion 132 for bundle 76 of signal lines is provided on the rear portion of connecting portion 135C. The distal end portion, inner conductors 81, and external conductor 82 of second bundle 76 of signal lines are fixed to second circuit board 54 by fixing resin 133.

An imaging apparatus according to the third embodiment further comprises third bundle 130 of signal lines. Inner conductors 131 of bundle 130 are connected to second conductive wire connecting portion 135B of first circuit board 54.

CCD 30 according to the third embodiment comprises two GND terminals. One GND terminal is connected to external conductor 82 of first bundle 74 of signal lines through first circuit board 54, and the other GND terminal is connected to external conductor 82 of second bundle 76 of signal lines through second circuit board 56.

As described above, connecting terminals need not be arranged at the two edge portions on the first and second boards, but can be arranged on desired portions thereon depending on a wiring pattern. In addition, the present invention is not limited to two bundles of power cables. For example, three or more bundles of power cables may be arranged.

Figure 30:
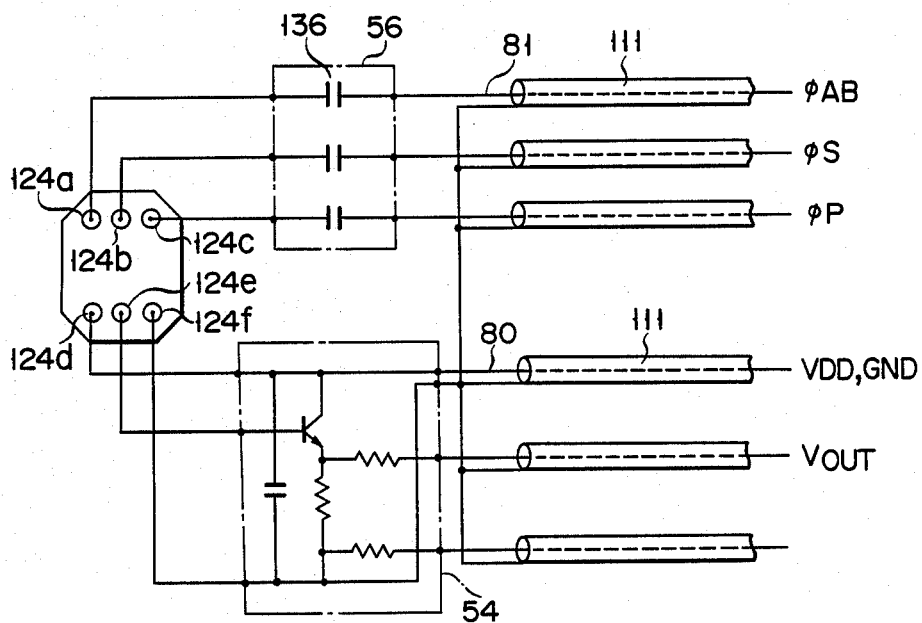
FIG. 30 is a schematic view showing a solid-state imaging device and electrical circuit according to another modification.

A modification of an electrical signal processing section having frame-sequential type CCD 30 will be described with reference to a diagram shown in FIG. 30.

In this modification, leads 124a to 124f of CCD 30 are respectively connected to shield wires 111 substantially in the same manner as in the CCD shown in FIG. 21. However, in this modification, leads 124a, 124b, and 124c of CCD 30 are connected to one terminal group of second circuit board 56, and inner conductors 81 of shield wires 111 (φAB, φS, and φP) are connected to the other terminal group of board 56. Capacitors 136 are respectively connected between one and the other terminal groups on second circuit board 56, respectively. Therefore, second circuit board 56 can perform signal processing, and output only an AC component.

With the imaging apparatus according to this modification as described above, the external terminals of the CCD are divided to two groups, and the respective terminal groups are connected to circuit boards for signal processing. However, signal exchange is not performed at all between the circuit boards connected to the two external terminal groups. For this reason, the camera head can be rendered compact in the same manner as in the above embodiments.

What is claimed is:

1. An imaging apparatus comprising:
  a camera head having
    (a) an objective optical system arranged on a front end portion of said camera head;
    (b) a solid-state imaging device arranged behind said objective optical system, said solid-state imaging device including a first external terminal group of terminals to or from which signals subjected to signal processing inside said camera head are input or output, and a second external terminal group, which is separated from said first external terminal group, and including terminals to or from which signals that are not subjected to signal processing inside said camera head are input or output, and
    (c) a first circuit board having at least two connecting terminal groups, one connecting terminal group being electrically connected to said first external terminal group;
  an electric cable having a first conductive wire group one end portion of which is connected to the other connecting terminal group of said circuit board, and a second conductive wire group one end portion of which is connected to said second external terminal group; and
  a camera control unit connected to the other end portion of each of said first and second conductive wire groups.

2. An apparatus according to claim 1, wherein said first circuit board is arranged to be parallel to a longitudinal axis of said camera lead.

3. An apparatus according to claim 2, wherein each of said first and second external terminal groups of said solid-state imaging device is arranged at least in a line, and the lines of said external terminals are arranged parallel to each other.

4. An apparatus according to claim 3, wherein each of said first and second external terminal groups is aligned in line, and is arranged to be perpendicular to the longitudinal direction of said camera head.

5. An apparatus according to claim 3, further comprising: a second circuit board having at least two connecting terminal groups and a wiring pattern portion, one connecting terminal group being connected to said second external terminal group, and the other connecting terminal group being connected to the one end portion of said second conductive wire group.

6. An apparatus according to claim 1, further comprising: a second circuit board having at least two connecting terminal groups and a wiring pattern portion, one connecting terminal group being connected to said second external terminal group, and the other connecting terminal group being connected to the one end portion of said second conductive wire group.

7. An apparatus according to claim 6, wherein said first and second circuit boards are arranged to be parallel to the longitudinal axis of said camera head.

8. An apparatus according to claim 7, wherein each of said first and second external terminal groups is aligned in line, and is arranged to be perpendicular to the longitudinal axis of said camera head.

9. An apparatus according to claim 6, wherein said first and second circuit boards are arranged parallel to each other.

10. An apparatus according to claim 7, wherein each connecting terminal at the other end of said second circuit board comprises a pipe-shaped lead.

11. An apparatus according to claim 6, wherein said first and second external terminal groups of said solid-state imaging device comprise flat leads, and said connecting terminals at the one end portions of said first and second circuit boards comprise L-shaped leads.

12. An apparatus according to claim 6, wherein said first and second external terminal groups comprise pin-shaped leads standing upright on a bottom surface of said solid-state imaging device, and said connecting terminals on the one end portion of said first circuit board comprise flat leads.

13. An apparatus according to claim 4, wherein said first and second circuit boards are arranged parallel to each other, and a filler is filled therebetween to integrally assemble said circuit boards.

14. An apparatus according to claim 1, wherein said camera head comprises a metal casing, and said casing is partially formed of a conductive film.

15. An apparatus according to claim 1, wherein said electric cable is separated into said first and second conductive wire groups near the rear end portion of said camera head.

16. An apparatus according to claim 15, wherein said electric cable comprises first and second bundles of conductive wires, said first and second bundles of conductive wires being terminated near the rear end portion of said camera head to serve as said first and second conductive wire groups.

17. An apparatus according to claim 1, wherein said electric cable comprises shield wires having inner and external conductors, said external conductor being electrically connected to a shield member near the rear end portion of said camera head.

18. An apparatus according to claim 1, wherein said first and second external terminal groups comprise pin-shaped leads standing upright on bottom surfaces of said solid-state imaging device, said connecting terminals at the one end portion of said first circuit board comprise flat leads, and said second conductive wire group is directly connected to said second external terminal group.

19. An apparatus according to claim 1, wherein said first external terminal group of said solid-state imaging device comprises flat leads, said one connecting terminal group of said first circuit board comprises flat leads, and said first circuit board is in contact with said solid-state imaging device so as to be perpendicular to each other.

20. An apparatus according to claim 1, wherein said first circuit board comprises a hybrid circuit board.

21. An apparatus according to claim 1, wherein said solid-state imaging device comprises a simultaneous type solid-state imaging device.

22. An apparatus according to claim 1, wherein said solid-state imaging device comprises a frame-sequential type solid-state imaging device.

23. An apparatus according to claim 1, further comprising an endoscope having an insertion section having a distal end member incorporating said camera head.

24. An apparatus according to claim 23, wherein said first and second conductive wire groups are divided over the entire length of the insertion section of said endoscope.

25. An apparatus according to claim 1, wherein said objective optical system has an optical element for diffracting an optical axis of said objective optical system, and said solid-state imaging device is arranged to be parallel to the axis of said camera head.

26. An apparatus according to claim 25, wherein said first and second external terminal groups are arranged at a proximal end portion of said solid-state imaging device.

27. An imaging apparatus comprising:
a camera head having
 (a) an objective optical system arranged on a front end portion of said camera head,
 (b) a solid-state imaging device arranged behind said objective optical system, said solid-state imaging device having first and second external terminal groups,
 (c) a first circuit board having at least two connecting terminal groups, one connecting terminal group being connected to said first external terminal group to perform signal processing, and
 (d) a second circuit board having at least two connecting terminal groups, one connecting terminal group being connected to said second external terminal group to perform signal processing different from said first circuit board;
an electric cable having a first conductive wire group one end portion of which is connected to the other connecting terminal group of said first circuit board, and a second conductive wire group one end portion of which is connected to the other connecting terminal group of said second circuit board; and
a camera control unit connected to the other end portion of each of said first and second conductive wire groups.

* * * * *